United States Patent
Bohm et al.

[11] Patent Number: 5,708,194
[45] Date of Patent: Jan. 13, 1998

[54] TEST GAS LEAK DETECTOR

[75] Inventors: Thomas Bohm, Cologne; Ulrich Dobler, Wermelskirchen, both of Germany

[73] Assignee: Leybold Aktiengesellschaft, Hanau, Germany

[21] Appl. No.: 702,645

[22] PCT Filed: Jan. 20, 1995

[86] PCT No.: PCT/EP95/00202

§ 371 Date: Sep. 6, 1996

§ 102(e) Date: Sep. 6, 1996

[87] PCT Pub. No.: WO95/25947

PCT Pub. Date: Sep. 28, 1995

[30] Foreign Application Priority Data

Mar. 24, 1994 [DE] Germany ............... 94 05 028 U

[51] Int. Cl.⁶ ............................................. G01M 3/20
[52] U.S. Cl. ............................................. 73/40.7
[58] Field of Search ................................. 73/40.7

[56] References Cited

U.S. PATENT DOCUMENTS

| | | | |
|---|---|---|---|
| 3,626,760 | 12/1971 | Briggs et al. | 73/40.7 |
| 3,939,695 | 2/1976 | Booth | 73/40.7 |
| 3,968,675 | 7/1976 | Briggs | 73/40.7 |
| 4,472,962 | 9/1984 | Mennenga | 73/40.7 |
| 5,343,740 | 9/1994 | Myneni | 73/40.7 |
| 5,561,240 | 10/1996 | Ochiai et al. | 73/40.7 |

*Primary Examiner*—Michael Brock
*Attorney, Agent, or Firm*—Harris Beach & Wilcox, LLP

[57] ABSTRACT

A leak detector (1) suitable for detecting leakage with a test gas connection (2), a test gas detector (3), a gas pump (4) and a test gas line (5) extending between the test gas connection (2) and the gas pump (4) and connected to the inlet (6) of the test gas detector (3) via a blockable branch; in order to shorten the response time, it is proposed that the line (7, 8) connecting the test gas line (5) to the inlet region (6) of the test gas detector be such that, during measurement, all of the gas flowing in the test gas line (5) essentially enters the inlet region (6) of the test gas detector (3).

6 Claims, 4 Drawing Sheets

TEST GAS LEAK DETECTOR

BACKGROUND OF THE INVENTION

The present invention relates to a leak detector suitable for detecting leakage with a test gas connection, a test gas detector, a gas pump and a test gas line extending between the test gas connection and the gas pump and connected to the inlet of the test gas detector via a blockable branch. With the branch open—measurement mode—a part of the gas which contains test gas in case of the presence of a leak, flowing through the test gas line, passes via the branch line into the test gas detector and it is recorded there.

In leak detectors of this kind, the response time, i.e. the time which elapses from the point of time when the gas enters into the test gas connection until the point of time when the test gas is recorded, is relatively long, at high pressures, in particular.

SUMMARY OF THE INVENTION

It is the task of the present invention to reduce the response time in a leak detector of the aforementioned kind.

This task is solved by the present invention through the characteristic features of the patent claims.

Through the proposed measures it is achieved that in the measurement operating mode substantially the entire quantity of the gas flowing through the test gas line enters directly into the test gas detector. Thus the response time is very much reduced, at higher pressures even by a factor of more than 10.

If the test gas detector comprises a mass spectrometer, and ahead of the mass spectrometer a high vacuum pump, preferably a turbomolecular pump through which the test gas passes upstream, then this invention has the effect that the gas flowing through the test gas line and thus the test gas contained in it arrives completely and directly at the discharge region of the high vacuum pump, so that the desired reduction in the response time can be attained.

Further advantages and details of the present invention shall be explained by referring to the design examples presented in drawing FIGS. 1 to 6.

DESCRIPTION OF THE INVENTION

Figure 1:
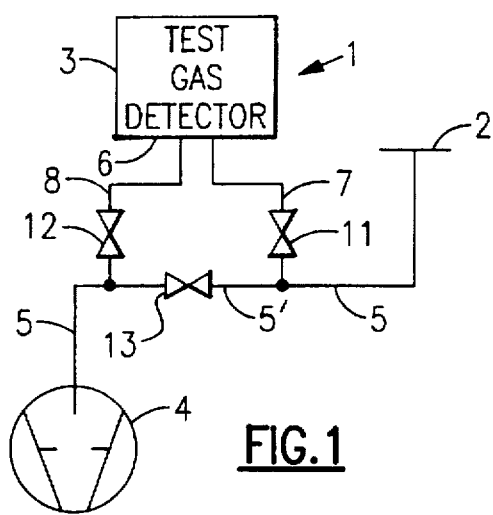
FIG. 1 is a schematic representation of a leak detection instrument according to a first embodiment of the present invention.

In the figures, the leak detection instrument is generally designated as 1, the test gas connection is designated as 2, the test gas detector as 3, the gas supply of backing pump as 4 and the test gas line extending between test gas connection 2 and backing pump 4 as 5. Test gas line 5 is connected to the inlet region 6 of the test gas detector 3 via two line sections 7 and 8.

In the design example according to drawing FIG. 1 the line sections 7 and 8 as well as the intermediate piece 5' of the test gas line 5 between the connections of line sections 7 and 8 to the test gas line 5 are each equipped with a 2/2 way valve 11, 12 or 13. In the measurement mode valves 11 and 12 are open, valve 13 is closed. The gas entering into test gas inlet 2 flows in its entirety directly into the inlet region 6 of the test gas detector 3. With closed valves 11, 12 and open valve 13—pumping operation—there exists the possibility of evacuating a test object or vacuum chamber connected to test gas connection 2. During standby mode the valves 11, 13 are closed and valve 12 is open.

Figure 2:
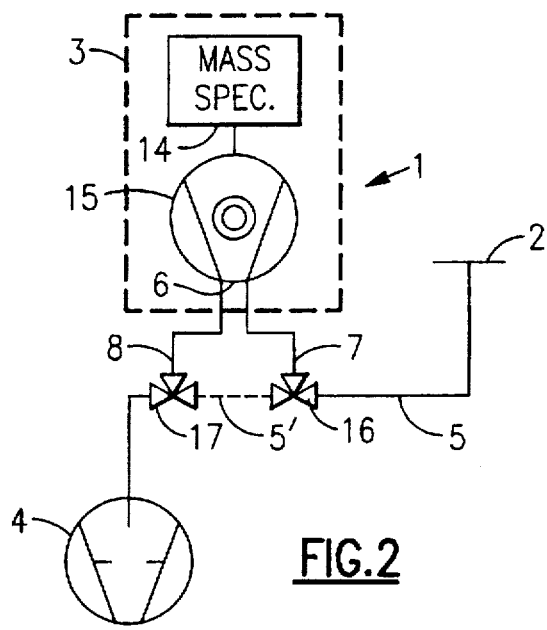
FIG. 2 is a schematic representation of a leak detection instrument in a measurement mode according to a second embodiment of the present invention.
Figure 3:
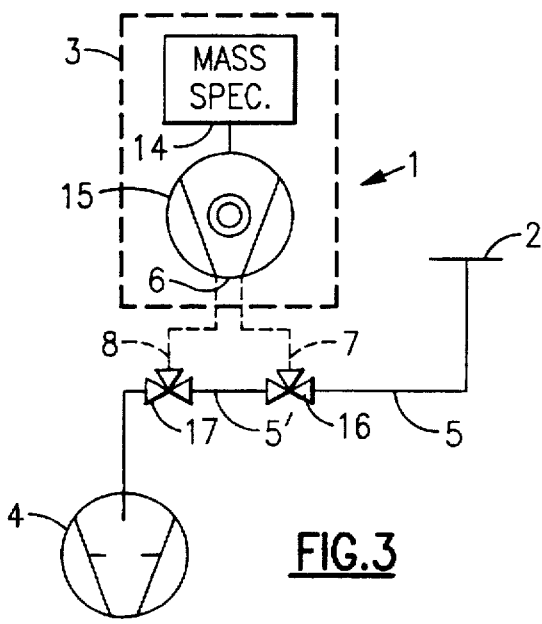
FIG. 3 is a schematic representation of the leak detection instrument of the second embodiment in a pumping mode.
Figure 4:
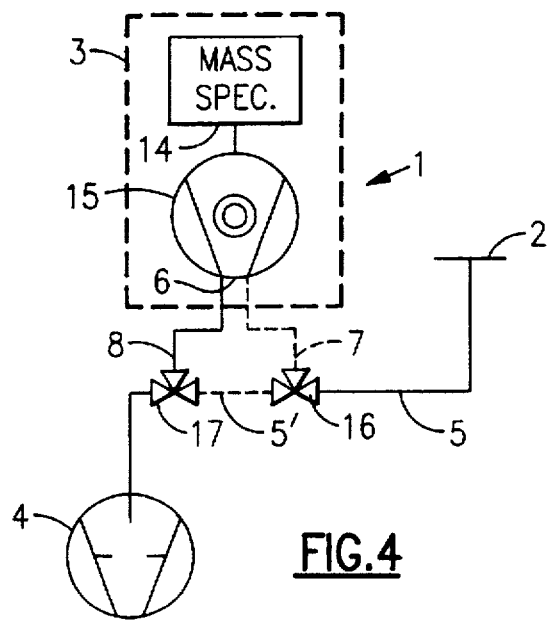
FIG. 4 is a schematic representation of the leak detection instrument of the second embodiment in a standby mode.

In the design examples according to drawing FIGS. 2 to 4 the test gas detector 3 comprises a mass spectrometer 14 and a high vacuum pump 15, preferably a turbomolecular vacuum pump. High vacuum pump 15 serves the purpose of maintaining the vacuum (about $10^{-4}$ mbar) required for operation of the mass spectrometer 14. In this design implementation the test gas—light gas, generally helium—flows upstream through the high vacuum pump. The inlet 6 of the test gas detector 3 thus represents at the same time the discharge of the high vacuum pump 15.

Instead of three 2/2 way valves 11, 12, 13 in line sections 7, 8, two 2/3 way valves 16, 17 are provided, which at the same time form the connections of line sections 7, 8 at test gas line 5. In the drawing FIGS. 2 to 4 the line sections 7, 8 and the intermediate piece 5' are represented by solid lines (open) or by dashed lines (blocked). Opening or blocking is in each case attained by the corresponding positions of valves 16, 17. Drawing FIG. 2 presents the measurement mode, drawing FIG. 3 the pumping mode and drawing FIG. 4 the standby mode.

Figure 5:
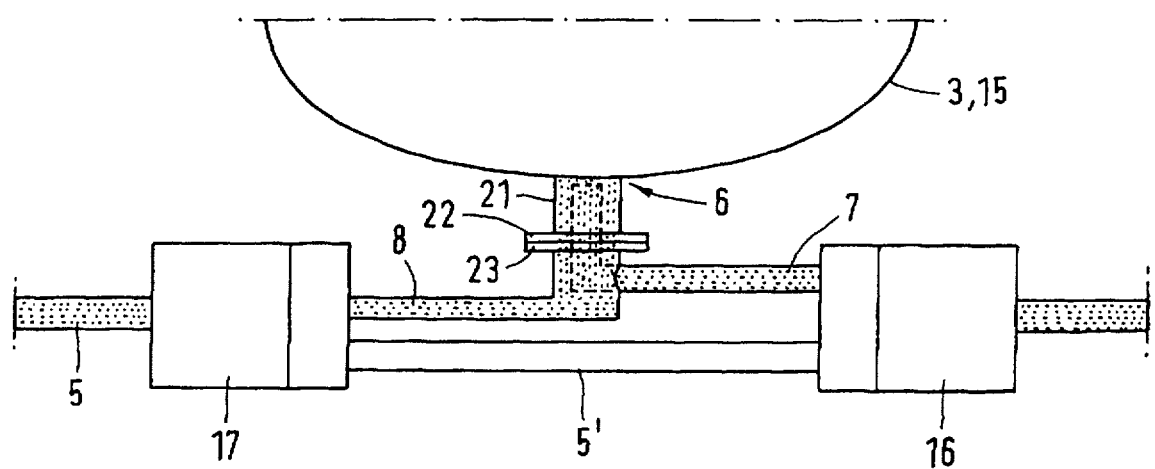
FIG. 5 shows a link in a measurement mode between a test gas line and a high vacuum pump according to an embodiment of the present invention.
Figure 6:
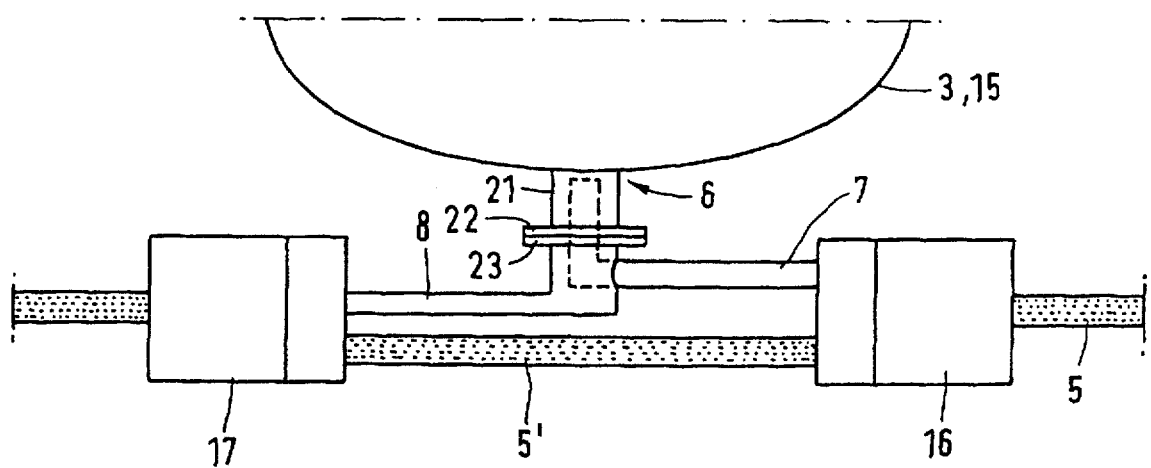
FIG. 6 shows a link in a pumping mode between a test gas line and a high vacuum pump according to an embodiment of the present invention.
Figure 1:
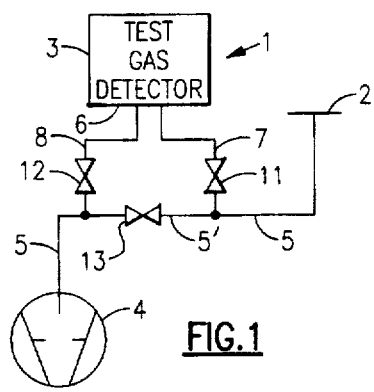
Figure 2:
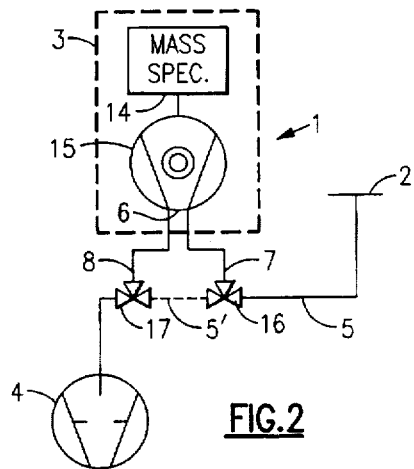
Figure 3:
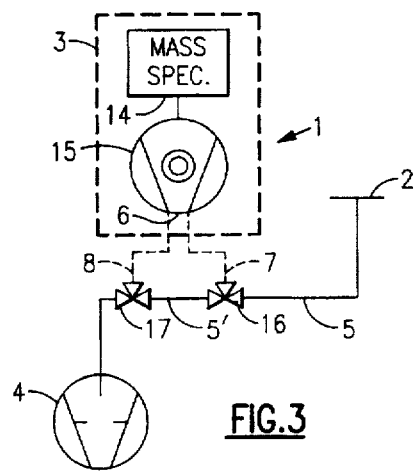
Figure 4:
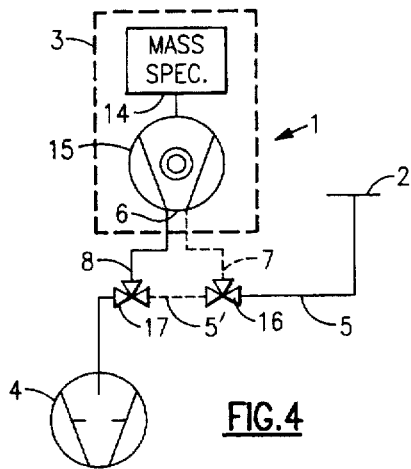
Figure 5:
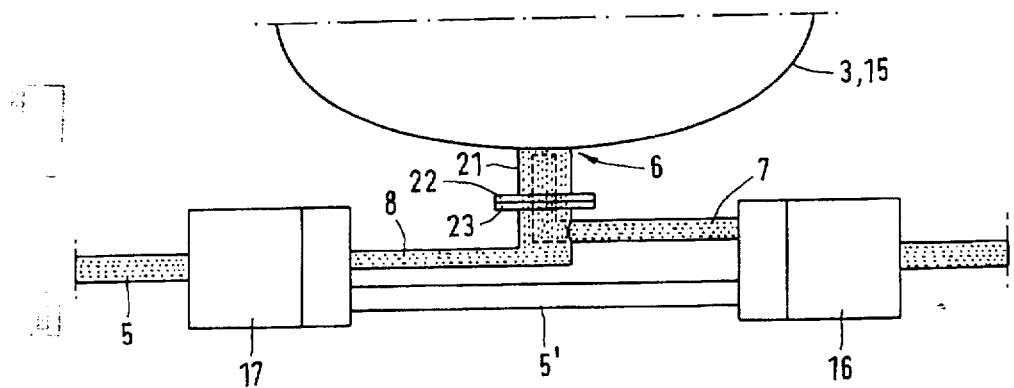
Figure 6:
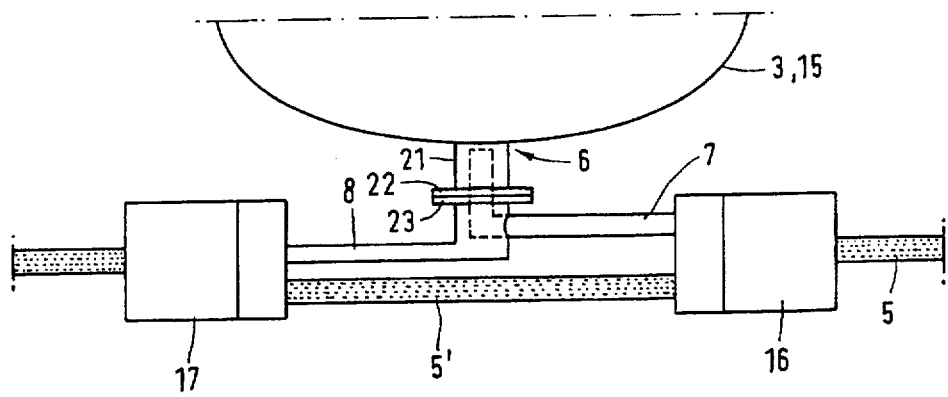

From drawing FIGS. 5 (measurement mode) and 6 (pumping mode) the preferred embodiment can be determined for the inlet region 6 of the test gas detector 3 (or the discharge 6 of the high vacuum pump 15). A connection port 21 with a flange 22 is part of the inlet 6 of test gas detector 3 (or the discharge 6 of the high vacuum pump 15). Line section 8—also equipped with a flange 23—is connected to this flange 22. At least in the region close to the flange, line 8 has a greater diameter compared to line section 7. In this region the line section 7 opens into line section 8. It passes through the region close to the flange of line 8 and ends at the level of line 8 opening into the test gas detector 3 or the high vacuum pump 15. This solution ensures that the entire quantity of gas flowing through the test gas line 5 arrives at the inlet 6 of the test gas detector 3 or the discharge 6 of the high vacuum pump 15.

What is claimed is:

1. Leak detecting apparatus, comprising:
    a test gas connection;
    a test gas detector, said test gas detector including a mass spectrometer connected to a high vacuum turbomolecular pump through which a test gas flows upstream, so that a discharge of said high vacuum turbomolecular pump forms an inlet to said test gas detector;
    a gas pump;
    a test gas line extending between the test gas connection and the gas pump; and
    blockable means connecting said test gas connection, said gas pump, and said inlet of said gas detector such that in a measurement mode said test gas connection and said gas pump are fluidly connected via said inlet, in a pumping mode said inlet is fluidly disconnected from both said test gas connection and said gas pump while said test gas connection and said gas pump are fluidly connected, and in a standby mode said test gas connection is fluidly disconnected from said inlet and said gas pump while said inlet and said gas pump are fluidly connected.

2. The apparatus of claim 1 wherein said blockable means includes a pair of branch lines connected between the test gas line and the inlet of the gas detector, said test gas line having an intermediate section extending between the two branch lines.

3. The apparatus of claim 2 wherein the two branch lines and the intermediate section of the test gas line each contain a 2/2 way valve.

4. The apparatus of claim 2 wherein each branch line is joined to the test gas line by a 2/3 way valve.

5. Leak detecting apparatus, comprising:
- a test gas connection;
- a test gas detector, said test gas detector including a mass spectrometer connected to a high vacuum turbomolecular pump through which a test gas flows upstream, so that a discharge of said high vacuum turbomolecular pump forms an inlet to said test gas detector;
- a gas pump;
- a test gas line extending between the test gas connection and the gas pump;
- blockable means connecting said test gas connection, said gas pump, and said inlet of said gas detector such that in a measurement mode said test gas connection and said gas pump are fluidly connected via said inlet, in a pumping mode said inlet is fluidly disconnected from both said test gas connection and said gas pump while said test gas connection and said gas pump are fluidly connected, and in a standby mode said test gas connection is fluidly disconnected from said inlet and said gas pump while said inlet and said gas pump are fluidly connected; and
- said blockable means including a pair of branch lines connected between said test gas line and said inlet of the gas detector, said test gas line having an intermediate section extending between said two branch lines, wherein the two branch lines each have a different cross sectional area at the inlet to the gas detector and the branch lines are mounted concentrically, one inside the other at the inlet to the gas detector.

6. The apparatus of claim 5 wherein the gas detector has a connection port containing a flange means and a large diameter branch line is connected to the flange means and a small diameter branch line passes through the flange means into the connection port.

* * * * *